(12) United States Patent
Fristoe

(10) Patent No.: US 8,733,711 B2
(45) Date of Patent: May 27, 2014

(54) CANNULA SUPPORT

(71) Applicant: Paula Fristoe, Redding, CA (US)

(72) Inventor: Paula Fristoe, Redding, CA (US)

( * ) Notice: Subject to any disclaimer, the term of this patent is extended or adjusted under 35 U.S.C. 154(b) by 0 days.

(21) Appl. No.: 13/722,923

(22) Filed: Dec. 20, 2012

(65) Prior Publication Data

US 2013/0327901 A1  Dec. 12, 2013

Related U.S. Application Data

(60) Provisional application No. 61/658,733, filed on Jun. 12, 2012.

(51) Int. Cl.
*A61M 16/06* (2006.01)

(52) U.S. Cl.
USPC ... 248/75; 248/51; 128/207.18; 128/DIG. 26; 128/864

(58) Field of Classification Search
CPC ............. A61M 25/02; A61M 2016/0672; A61M 2210/0618; A61M 2230/005; A61M 2025/0226; A61M 2025/026; A62B 9/04
USPC ............... 248/75, 51; 128/207.18, 207.17, 128/DIG. 26, 864
See application file for complete search history.

(56) References Cited

U.S. PATENT DOCUMENTS

| | | | | |
|---|---|---|---|---|
| 3,266,760 A | * | 8/1966 | Edelman | 248/51 |
| 3,288,136 A | * | 11/1966 | Lund | 604/180 |
| 3,973,556 A | * | 8/1976 | Fleischhacker et al. | 600/585 |
| 4,406,283 A | * | 9/1983 | Bir | 128/207.18 |
| 4,699,139 A | * | 10/1987 | Marshall et al. | 128/207.18 |
| 4,817,921 A | * | 4/1989 | Stevenson | 267/33 |
| 4,949,733 A | * | 8/1990 | Sampson | 128/864 |
| 5,025,805 A | * | 6/1991 | Nutter | 128/207.18 |
| 5,398,895 A | * | 3/1995 | Whetherhult et al. | 248/51 |
| 6,071,279 A | * | 6/2000 | Whayne et al. | 606/41 |

* cited by examiner

*Primary Examiner* — Anita M King
(74) *Attorney, Agent, or Firm* — Lowry Blixseth LLP; Scott M. Lowry

(57) ABSTRACT

The cannula support includes a helical cord flexible along its length to permit selective axial displacement of adjacent coils for insertion of a cannula tube therein and a breathable material that permits prolonged skin contact substantially without irritation. Furthermore, the cannula support includes an exterior surface having a coefficient of friction substantially preventing sliding movement along the length of the cannula tube when mounted thereon.

14 Claims, 1 Drawing Sheet

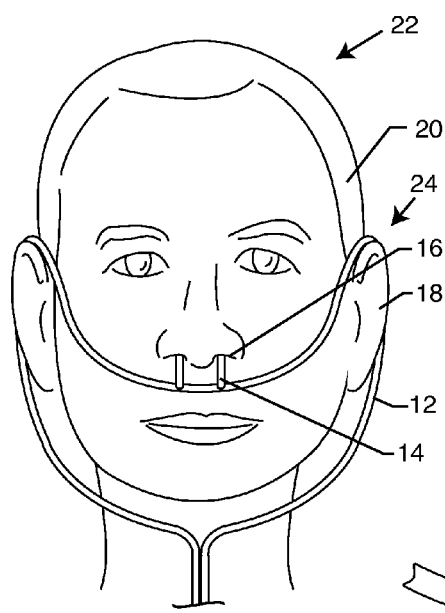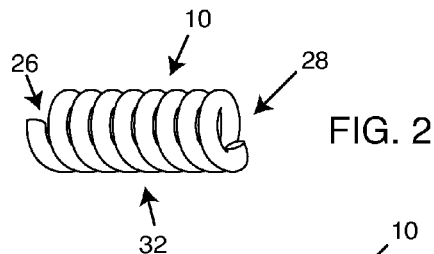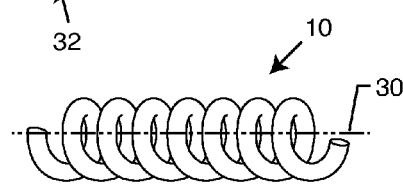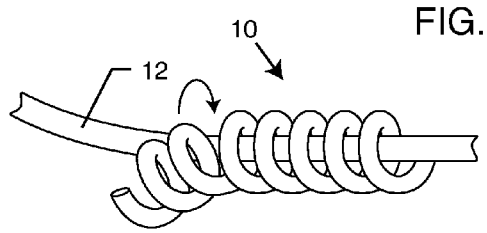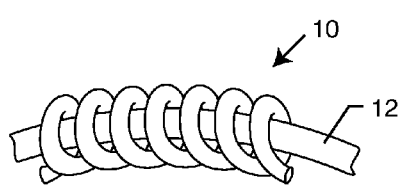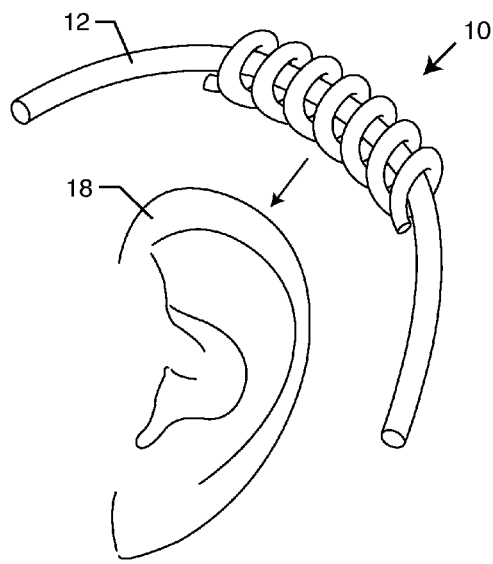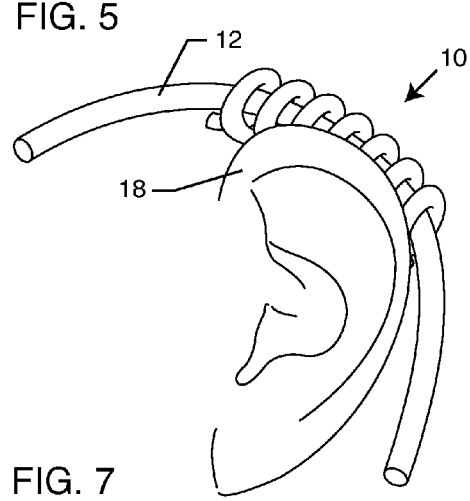

CANNULA SUPPORT

BACKGROUND OF THE INVENTION

The present invention is directed to a support device for a cannula. More specifically, the present invention is directed to a cannula support that includes a plurality of interlocking fibers spiral-bound together in a manner that permits selective attachment to a flexible plastic cannula tube for providing cushioned and molded support in and around the ear, and preventing irritation known to be induced by plastic-to-skin contact from the flexible tube.

A cannula is a somewhat slender and elongated tube that can be used to deliver or remove fluids from the body. In this respect, the more specific nasal cannula or oral-nasal cannula is a device used to deliver supplemental oxygen to a patient in need of respiratory help. At one end, the flexible tube may extend from or attach to a device that might include an oxygen tank, a portable oxygen generator, or a wall connection in a hospital that delivers oxygen via a flow meter. At the other end, the flexible tube terminates into one or more open-ended ports designed to be inserted into the nostrils and/or the mouth. Oxygen flows from the source, through the tube and out through the open-ended ports as a means to supplement breathing. The open-ended ports may vary in size depending on the desired flow rate of oxygen.

As generally shown in FIG. 1, the cannula is positioned to provide oxygen through one or more ports positioned near the wearer's nostrils. The flexible plastic tube of the cannula wraps around the cheeks toward the ears. In most cases, the flexible plastic tube of the cannula sits in the space or channel formed between the ear and the scalp—doing so can cause skin irritation, as described in more detail below. Furthermore, the flexible plastic tube of the cannular wraps around behind the ear and comes back toward the front area of the neck, by the chin, for travel back to the oxygen source. In this configuration, the cannula typically does not inadvertently fall out of the patient's nostrils and/or mouth through casual movement.

The problem is that the plastic material of the cannula typically remains compressed against the skin between the ear and the scalp and after a while the plastic material tends to stick to the skin. Constant contact can cause indentations in the skin, redness, sores or other skin irritations, especially if the skin-to-plastic contact does not allow the skin to breathe underneath. In this respect, if the flexible plastic tube sticks to the skin, the wearer can tear the skin in and around the ear when the cannula moves (e.g., by turning your head). This problem is exacerbated by the fact that nasal cannula are often used or worn by elderly patients whose skin may produce insufficient quantities of oil to keep the external area of the skin lubricated in a manner that prevents or lessens sticking. Placing the plastic tube on open sores or against torn skin is particularly painful and does not allow for healing.

As such, several products have been developed to help solve the problem of skin irritation around the ears associated with cannula usage. But, these products have drawbacks of their own. For example, the E-Z Wrap Soft Foam Ear Protectors for Oxygen Nasal Cannulas (1-Pair), made by Salter Labs of 100 W. Sycamore Road, Arvin, Calif. 93203, are 3-inch soft closed-cell foam tubes having an inner diameter relatively larger than the external diameter of the cannula tube such that the cannula tube can be inserted therein through a slit down one side of the foam tube. The foam tube covers the portion of the plastic cannula tubing that sits over a portion of the ear when the oxygen cannula is worn. In this respect, the E-Z Wraps are designed to improve comfort and help prevent chafing and soreness. But, this product does not stay in place and tends to easily slip down along a portion of the cannula tube such that it is no longer in position. Additionally, the straight and relatively stiff structure of the foam tube has a tendency to dislodge from the curved area of the ear because the straight foam tube is non-conforming thereto. This too may cause the E-Z Wrap to slide down the flexible plastic tube of the cannula such that it is no longer in a position to protect the ear from the irritating plastic flexible tube of the cannula. As a result, this product may be a nuisance or not work at all, especially for active users. Some solutions have included applying an adhesive, such as tape, to prevent such movement, but this is not ideal.

Accordingly, there is a need in the art for a cannula support that is flexible so as to be selectively attachable to the cannula, may be adjusted or bent to fit or conform to the exterior surface of the curved area of the ear where the cannula sits and is supported when worn, is comfortable, and prevents substantial skin-to-plastic contact that may otherwise cause skin irritation. The present invention fulfills these needs and provides further related advantages.

SUMMARY OF THE INVENTION

The cannula support disclosed herein includes a helical cord flexible along its length to permit selective axial displacement of adjacent coils for insertion of a cannula tube therein. In this respect, the support preferably includes a plurality of elastic coils that conform to a curved exterior surface of a cannula tube by expanding along a major or outer diameter and contracting without bunching along a minor or inner diameter of the curved cannula tube. To permit prolonged skin contact without substantial irritation thereof, the helical cord is preferably made from a breathable material such as a polyester outer sheath made from a series of interwoven spiral-bound fibers forming a porous material that permits moisture to vent from the skin surface. This aspect of the cannula support is advantageous over the prior art in that known devices cause irritation, as described herein. Furthermore, this outer sheath of the cannula support preferably has a coefficient of friction that substantially prevents sliding movement along the length of the cannula tube when mounted thereon.

In an alternative embodiment, the helical cord includes an inner diameter relatively smaller than the exterior surface of the cannula tube. This feature further prevents unwanted sliding movement along the length of the curved exterior surface of the cannula tube. In this respect, the plurality of coils may taper in diameter along a common axis of the helical cord to provide a better fit. To this extent, the taper may be in a conical shape. Alternatively, for example, the helical cord may be made from at least a portion of a curled shoelace, or at least have a common shape therewith. The helical cord should be of a thickness sufficient to bias the cannula tube away from skin contact when the cannula tube is worn and may include an inner cord made from cotton, polyester, or other like material surrounded by the softer or relatively more pliable polyester outer sheath. The helical cord should be sized for easy slide-fit reception between a wearer's ear and scalp.

In an alternative embodiment, the cannula support includes a helical cord having a plurality of elastic coils that conform to a curved exterior surface of a cannula tube by expanding along a major diameter and contracting without bunching along a minor diameter. The helical cord is flexible along its length to permit selective axial displacement of adjacent coils for insertion of the cannula tube therein. Preferably, the helical cord is made from a breathable material that permits prolonged skin contact substantially without causing irritation thereof and includes a thickness sufficient to bias the cannula tube away from skin contact when the cannula tube is worn.

Further to this embodiment, the helical cord may include an inner diameter relatively smaller than the exterior surface of the cannula tube to enhance the fit thereto. This may be especially beneficial when used in conjunction with a helical cord that includes a inner cord made from cotton, polyester, or other like material and a polyester outer sheath having a series of interwoven spiral-bound fibers forming a porous material permitting moisture to vent from the skin—a polyester outer sheath having a coefficient of friction designed to substantially prevent sliding movement of the cannula support along the length of the cannula tube when mounted thereon. Further to this extent, the plurality of coils may taper in diameter along a common axis of the helical cord to form, for example, a conical shape. In one embodiment, the helical cord may be made from at least a portion of a curled shoelace and is preferably sized for slide-fit reception between a wearer's ear and scalp.

In an additional embodiment, the cannula support includes a helical cord that includes at least a portion of a curled shoelace flexible along its length to permit selective axial displacement of adjacent coils for insertion of a cannula tube therein. The helical cord is preferably of a thickness sufficient to bias the cannula tube away from skin contact when the cannula tube is worn. To this extent, the helical cord is also sized for slide-fit reception between a wearer's ear and scalp and is made from a breathable material having a coefficient of friction substantially preventing sliding movement along the length of the cannula support while permitting prolonged skin contact substantially without irritation when mounted thereon. In this embodiment, the helical cord also includes a plurality of elastic coils that taper in diameter along a common axis and conform to a curved exterior surface of the cannula tube by expanding along a major diameter and contracting along a minor diameter. The helical cord may include an inner cord made from cotton, polyester, or other like material and a polyester outer sheath having an inner diameter relatively smaller than the exterior surface of the cannula tube. The polyester outer sheath may include a series of conically-shaped interwoven spiral-bound fibers forming a porous material permitting moisture to vent from the skin.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a perspective view illustrating a patient wearing a nasal-cannula including a flexible tube wrapped around an ear;

FIG. 2 is a perspective view of a cannula support as disclosed herein;

FIG. 3 is a perspective view of the cannula support of FIG. 2 partially uncoiled;

FIG. 4 is an environmental perspective view illustrating attachment of the cannula support to the flexible tube;

FIG. 5 is a perspective view illustrating the cannula support fully attached to the flexible tube;

FIG. 6 illustrates placement of the cannula support behind the ear; and

FIG. 7 illustrates the cannula support positioning the flexible tube of the cannula in substantial non-contact relation with the skin in and around the ear.

DETAILED DESCRIPTION OF THE PREFERRED EMBODIMENT

As shown in the drawings for purposes of illustration, the present invention for a cannula support is referred to generally by the reference number 10 in FIGS. 2-7. In this respect, the support 10 may be used in association with a cannula that consists of a somewhat slender and elongated tube 12 (FIG. 1) that extends from a device such as an oxygen tank, a portable oxygen generator, or a wall connection in a hospital that delivers oxygen via a flow meter (not shown) at one end to one or more open ended branches or ports 14 at the other end designed to be inserted into, for example, a nostril 16 to deliver supplemental oxygen to a patient in need of respiratory help. Oxygen flows from the source, through the flexible tube 12 and out through one or more of the open-ended branches or ports 14 as a means to supplement breathing. The open-ended branches or ports 14 may vary in size depending on the desired flow rate.

As generally shown in FIG. 1, the branches or ports 14 of the cannula flexible tube 12 are positioned near the nostrils 16 to provide oxygen thereto. From here, the cannula flexible tube 12 wraps around the cheeks of the wearer 22 toward the ears 18. As such, the flexible plastic tube 12 may extend into a space or channel 24 formed between the head 20 and a portion of the outwardly extending ear 18. The cannula flexible tube 12 then wraps around the ear 18, comes back toward the front of the neck by the chin and travels back to the oxygen source. The tube 12 is typically made from a somewhat flexible plastic material that can be manipulated in a manner that allows conformity around the wearer's facial features, for example the exterior curvature of the face and around the ear 18, to streamline the fit of the cannula to the wearer 22 as shown in FIG. 1.

The support 10 disclosed herein is a supplemental attachment for the cannula flexible tube 12 as it is designed to reduce or eliminate the aforementioned problems associated with skin-to-plastic contact with the flexible tube 12. That is, the support 10 helps reduce indentations that may form in and around the skin from constant contact with the flexible tube 12, reduce redness, sores or other skin irritations, and reduce or eliminate tearing of the skin resultant from the flexible tube 12 sticking to the skin.

FIG. 2 illustrates one embodiment of the support 10 in the form of a curled or coiled cord that may be formed by winding strips of material around a cylinder to create the shown helical shape. Preferably, the support 10 comprises a form of elastic material (e.g., polyester) that permits stretching or uncoiling when loaded (FIG. 3), while also returning to its natural length (FIG. 2) when unloaded. The helical shape of the support 10 shown in FIGS. 2-7 produces a smooth three-dimensional curve with each coil initially aligned along a common central axis 30 (FIG. 3). While the support 10 in FIGS. 2-7 is substantially cylindrical in shape, it could be made into a conical shape by winding it around a cone, for example. In this respect, the ends 26, 28 of the support 10 may taper inwardly toward the exterior circumference of the flexible tube 12 to provide a tighter fit thereto at each of the ends 26, 28. This embodiment may prevent the support 10 from sliding along the length of the flexible tube 12, as is problematic with the E-Z Wraps.

The shape, structure and materials of the support 10 are, in one embodiment, comparable to or the same as the outer polyester material of curly or spiral shoelaces. In this respect, the support 10 may similarly include a tight inner core that helps maintain or form the outer polyester material into the spiral or helical shape of the support 10. The outer layer preferably includes the aforementioned polyester material, but a person of ordinary skill in the art will readily recognize that the outer layer of the support 10 may be made from various types of materials, such as cotton, nylon, polyester, spandex, etc. Of course, the support 10 may include only the outer polyester material or both the outer polyester material with the harder inner core. In this respect, the outer polyester material may be configured to naturally coil itself, as disclosed herein.

The elasticity of the support 10 allows it to be bent, curved, extended, retracted, etc. as generally shown in FIGS. 3-7. In this respect, material selection is important so that the support 10 can adequately conform to the outer curved surface of the ear (FIGS. 6 and 7) to bias the plastic tube 12 away from contacting the skin. The support 10 may also enhance the positional stability of the cannula in and around the ear 18 by increasing the traction therewith while comfortably contacting the skin without causing irritation thereto. The substantially spiral or helical shape of the support 10 made from polyester (or a comparable material) accomplishes these objectives.

For instance, FIG. 4 illustrates the support 10 being bent and turned around the exterior of the flexible tube 12. In this embodiment, the inner diameter formed by the helical structure of the support 10 is approximately the same size as the outer diameter of the flexible tube 12. This allows the wearer 22 to comfortably slide or spiral bind the support 10 along the length of the flexible tube 12 to properly locate and place the support 10 to attain a comfortable fit behind the ear 18, as shown in FIG. 7. The inner diameter of the support 10 may, alternatively, be somewhat smaller than the outer diameter of the flexible tube 12 to enhance frictional contact therebetween during use. This, of course, will tend to inhibit movement of the support 10 along the length of the flexible tube 12 relative to a support 10 with a larger diameter. In another alternative embodiment, the support 10 may have a somewhat larger inner diameter at or near its mid-section 32 (generally shown in FIG. 2) that terminates at respective conically shaped ends 26, 28. This embodiment may provide enhanced contact at each end 26, 28, while allowing greater adjustability in the larger diameter mid-section 32.

As shown in FIG. 5 relative to FIG. 4, the support 10 is flexible enough to be wound around the exterior of the flexible tube 12. In one embodiment, the support 10 attached to the flexible tube 12, as shown in FIG. 5, may be a two inch piece of curled shoelace with the harder interior cord removed. Once attached, the wearer may manipulate the shape and placement of the flexible tube 12 with the support 10 mounted thereto. In this regard, FIG. 5 illustrates the support 10 partially curved and shaped to conform to the curved exterior surface of the ear 18. Placement behind the ear 18 in this manner, and as shown in FIG. 7, permits the support 10 to bias the inner plastic flexible tube 12 away from contacting the skin in and around the ear 18 to prevent or stop the aforementioned skin irritations. Since the support 10 is curled around the exterior of the flexible tube 12, it does not fall off when bent around the ear 18. In this respect, the curled helical shape not only grips to portions of the flexible tube 12 to prevent slippage, as described above, but it also provides enhanced traction against the skin in the area in and around the ear 18. Additionally, the polyester clothing-type material made from a series of interwoven spiral-bound fibers allows the skin to breath underneath (similar to clothing) and does not have the same abrasive surface interaction with the skin as does the plastic material of the flexible tube 12. Accordingly, the support 10 stays on the flexible tube 12 until purposefully unwrapped, provides adequate stability, and causes virtually no skin irritation.

Moreover, the spiral or helical shape of the interwoven fibers of the support 10 provides the flexibility necessary to conform to the outer curvature in and around the ear 18 while providing sufficient traction against the skin without irritation. In this respect, each of the coils of the support 10 may expand (FIG. 2) or contract (FIG. 3) and bend along the central axis 30 thereof (FIG. 3 relative to FIGS. 6-7). A solid foam material, such as the E-Z Wrap design, is unable to flex in this manner because the solid material bunches and prevents interior curving, and otherwise does not permit exterior stretching in the same manner that a series of spaced apart and flexible/bendable helical coils provide. This shape and structure of the support 10 further enhances gripping action in and around the ear 18 so that the support 10 and the flexible tube 12 do not slip or slide out from this space or channel 24 when worn by the wearer 22. That is, the coils are able to bend with the flexible tube 12 so as to remain in some constant frictional contact therewith such that each of the individual coils are no longer necessarily aligned with the central axis 30.

Several individuals using a nasal-cannula have used the support 10 disclosed herein as an alternative to using bandages to cover areas around the ears that were torn and bleeding from the irritation of the cannula flexible tube 12. In each case, the individual was able to use the support 10 for at least six months without having any of the aforementioned problems associated with skin irritation in and around the ears. Of course, the support 10 would be beneficial to those who use oxygen, and especially those who must be on oxygen all day and all night.

Although several embodiments have been described in detail for purposes of illustration, various modifications may be made without departing from the scope and spirit of the invention. Accordingly, the invention is not to be limited, except as by the appended claims.

What is claimed is:

1. A cannula support, comprising:
    a helical cord flexible along its length to permit selective axial displacement of adjacent coils for insertion of a cannula tube therein, the helical cord comprising a series of interwoven spiral-bound fibers forming a porous material permitting moisture to vent from the skin;
    wherein the helical cord comprises a breathable material to permit prolonged skin contact substantially without irritation and a coefficient of friction substantially preventing sliding movement along the length of the cannula tube when mounted thereon.

2. The cannula support of claim 1, wherein the helical cord comprises a plurality of elastic coils that conform to a curved exterior surface of the cannula tube by expanding along a major diameter and contracting without bunching along a minor diameter.

3. The cannula support of claim 2, wherein the helical cord includes an inner diameter relatively smaller than the exterior surface of the cannula tube.

4. The cannula support of claim 2, wherein the plurality of coils taper in diameter along a common axis of the helical cord.

5. The cannula support of claim 4, wherein the helical cord comprises a conical shape.

6. The cannula support of claim 1, wherein the helical cord comprises a thickness sufficient to bias the cannula tube away from skin contact when the cannula tube is worn.

7. The cannula support of claim 1, wherein the helical cord comprises at least a portion of a curled shoelace.

8. The cannula support of claim 1, wherein the helical cord is sized for slide-fit reception between a wearer's ear and scalp.

9. A cannula support, comprising:
a helical cord including a plurality of elastic coils that conform to a curved exterior surface of a cannula tube by expanding along a major diameter and contracting without bunching along a minor diameter, the helical cord being flexible along its length to permit selective axial displacement of adjacent coils for insertion of the cannula tube therein, wherein the helical cord comprises a polyester sheath having a series of interwoven spiral-bound fibers forming a porous material permitting moisture to vent from the skin;
wherein the helical cord comprises a breathable material that permits prolonged skin contact substantially without irritation and has a thickness sufficient to bias the cannula tube away from skin contact when the cannula tube is worn.

10. The cannula support of claim 9, wherein the helical cord includes an inner diameter relatively smaller than the exterior surface of the cannula tube and the plurality of coils taper in diameter along a common axis of the helical cord.

11. The cannula support of claim 10, wherein the helical cord comprises a conical shape.

12. The cannula support of claim 9, wherein the helical cord comprises at least a portion of a curled shoelace and is sized for slide-fit reception between a wearer's ear and scalp.

13. The cannula support of claim 11, wherein the polyester outer sheath includes a coefficient of friction substantially preventing sliding movement of the cannula support along the length of the cannula tube when mounted thereon.

14. A cannula support, comprising:
a helical cord comprising at least a portion of a curled shoelace and flexible along its length to permit selective axial displacement of adjacent coils for insertion of a cannula tube therein, wherein the helical cord comprises a thickness sufficient to bias the cannula tube away from skin contact when the cannula tube is worn;
wherein the helical cord comprises a plurality of elastic coils that taper in diameter along a common axis and conform to a curved exterior surface of the cannula tube by expanding along a major diameter and contracting without bunching along a minor diameter;
wherein the helical cord includes an inner cord surrounded by a relatively softer polyester outer sheath having an inner diameter relatively smaller than the exterior surface of the cannula tube, the polyester outer sheath comprising a series of conically-shaped interwoven spiral-bound fibers forming a porous material permitting moisture to vent from the skin; and
wherein the helical cord is sized for slide-fit reception between a wearer's ear and scalp and comprises a breathable material having a coefficient of friction substantially preventing sliding movement along the length of the cannula support while permitting prolonged skin contact substantially without irritation when mounted thereon.

\* \* \* \* \*